United States Patent [19]

Patno et al.

[11] Patent Number: 5,538,405
[45] Date of Patent: Jul. 23, 1996

[54] PERISTALTIC PULSE PUMPING SYSTEMS AND METHODS

[75] Inventors: Timothy J. Patno, Mundelein; Richard I. Brown, Northbrook; William H. Cork, Lake Bluff, all of Ill.

[73] Assignee: Baxter International Inc., Deerfield, Ill.

[21] Appl. No.: 269,933

[22] Filed: Jul. 1, 1994

[51] Int. Cl.[6] .................................................. F04B 43/08
[52] U.S. Cl. .......................................... 417/326; 417/474
[58] Field of Search ............................. 417/477.1, 326, 417/474, 476

[56] References Cited

U.S. PATENT DOCUMENTS

| | | | |
|---|---|---|---|
| 3,938,909 | 2/1976 | Willock | 417/477.1 |
| 4,108,575 | 8/1978 | Schäl | 417/53 |
| 4,210,409 | 7/1980 | Child | 417/241 |
| 4,221,543 | 9/1980 | Cosentino et al. | 417/22 |
| 4,365,728 | 12/1982 | Tokorozawa et al. | 417/477.1 |
| 4,468,219 | 8/1984 | George et al. | 604/66 |
| 4,492,531 | 1/1985 | Kenji et al. | 417/279 |
| 4,496,342 | 1/1985 | Banko | 604/27 |
| 4,498,850 | 2/1985 | Perlov et al. | 417/322 |
| 4,549,860 | 10/1985 | Yakich | 417/475 |
| 4,662,829 | 5/1987 | Nehring | 417/395 |
| 4,697,989 | 10/1987 | Perlov et al. | 417/53 |
| 4,735,726 | 4/1988 | Duggins | 210/637 |
| 4,755,168 | 7/1988 | Romanelli et al. | 417/477.1 |
| 4,910,682 | 3/1990 | Wolff et al. | 364/510 |
| 4,969,808 | 11/1990 | Tsukada | 417/477.1 |
| 5,024,347 | 6/1991 | Baldwin | 417/477.1 |
| 5,083,908 | 1/1992 | Gagnebin et al. | 417/477 |
| 5,098,261 | 3/1992 | Bertoncini | 417/475 |
| 5,125,891 | 6/1992 | Hossain et al. | 604/34 |
| 5,195,960 | 3/1993 | Hossain et al. | 604/34 |

*Primary Examiner*—Peter Korytnyk
*Attorney, Agent, or Firm*—Daniel D. Ryan; Bradford R. L. Price; Joseph B. Barrett

[57] ABSTRACT

A peristaltic pumping apparatus and associated method to control power to the pump rotor to establish, during a preestablished first time period, a selected first angular velocity and sequentially establishing during a preestablished second time period immediately following the first time period a second angular velocity different than the first angular velocity. In this fashion, the apparatus and method achieve flow rates well below the minimum continuous flow rate of the rotor.

1 Claim, 15 Drawing Sheets

5,538,405

PERISTALTIC PULSE PUMPING SYSTEMS AND METHODS

FIELD OF THE INVENTION

The invention relates to blood processing systems and apparatus.

BACKGROUND OF THE INVENTION

Today people routinely separate whole blood by centrifugation into its various therapeutic components, such as red blood cells, platelets, and plasma.

Conventional blood processing methods use durable centrifuge equipment in association with single use, sterile processing systems, typically made of plastic. The operator loads the disposable systems upon the centrifuge before processing and removes them afterwards.

Conventional automated blood processing methods typically entail a range of different fluid flow rates. Relatively high flow rates are required to circulate blood during processing, as well as to circulate ancillary fluids for priming before use and rinsing after use. On the other hand, relatively low flow rates are required to supply anticoagulant.

One approach is to provide dedicated pumps, some to meet high flow volume requirements, and others to meet low flow volume requirements.

The approach that the invention takes is different. A principal objective of the invention is to meet both high and low flow requirements with a single pump.

SUMMARY OF THE INVENTION

The invention makes possible the operation of the same peristaltic pump to provide both high and low flow conditions in a relatively inexpensive and straightforward way.

One aspect of the invention provides a peristaltic pumping apparatus and associated method. The pumping apparatus comprises a peristaltic pumping element that includes a pump rotor carrying a rotor and a drive mechanism for rotating the rotor. The apparatus and method control power to the drive mechanism to establish, during a preestablished first time period, a selected first angular velocity. The apparatus and method sequentially establish during a preestablished second time period immediately following the first time period a second angular velocity different than the first angular velocity. By preselecting angular velocities to switch between and by timing the periods of switching, the apparatus and method achieve a range of desired low flow rates.

In a preferred embodiment, during the first time period, the pump rotor revolves less than one complete revolution. During the second period, the second angular velocity is zero so that rotation of the pump rotor ceases.

According to another aspect of the invention, the apparatus and method sequentially operate the drive mechanism in a continuous mode and in an intermittent mode. In the continuous mode, the apparatus and method control power to the drive mechanism to continuously rotate the pump rotor to provide a first selected flow rate. In the intermittent mode, the apparatus and method provide a second selected flow rate less than the first selected flow rate by controlling power to the drive mechanism to establish, during a preestablished first time period, a selected first angular velocity and sequentially establishing during a preestablished second time period immediately following the first time period a second angular velocity different than the first angular velocity.

The features and advantages of the invention will become apparent from the following description, the drawings, and the claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
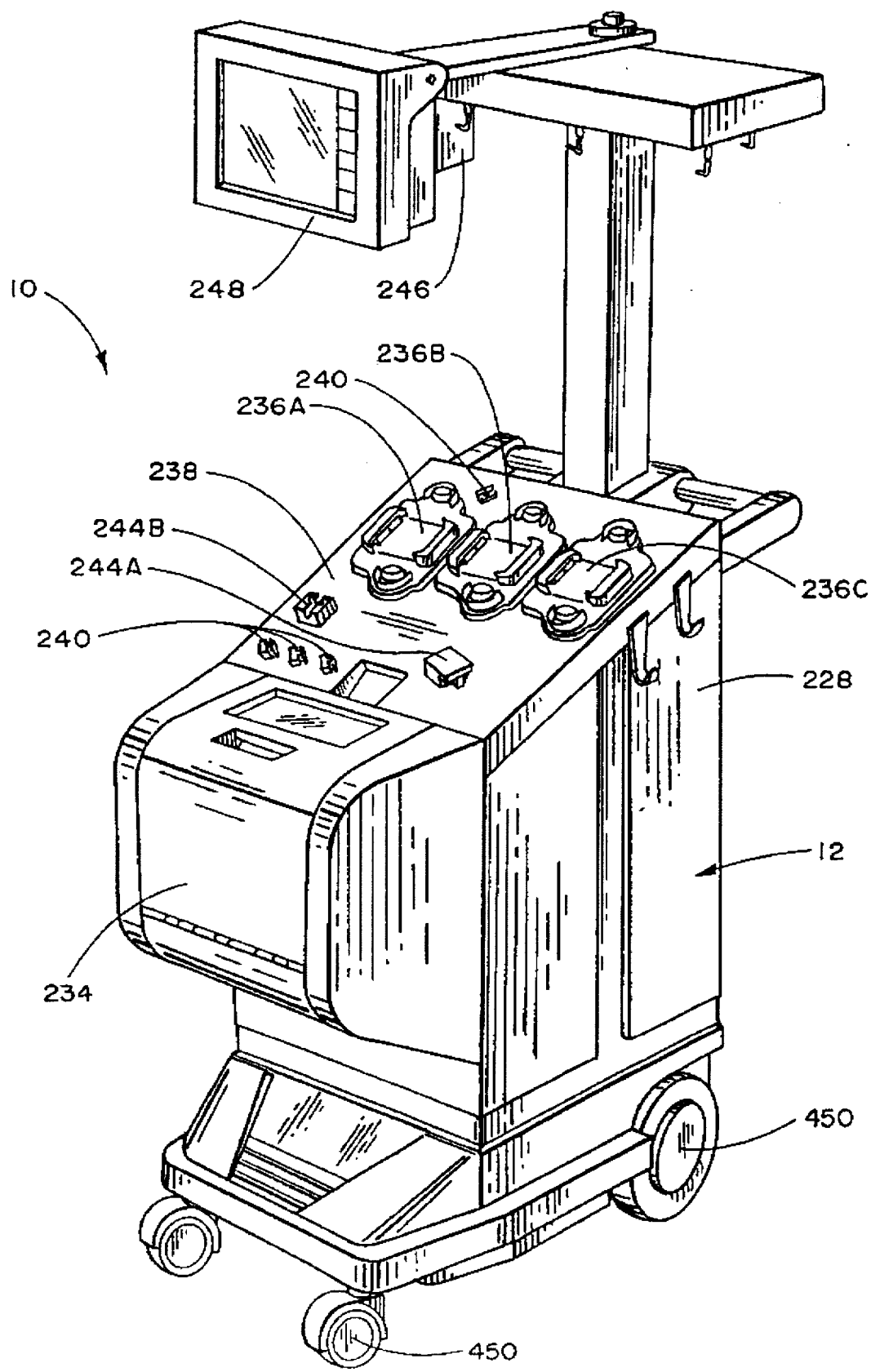
FIG. 1 is a perspective view of a centrifugal assembly that embodies the features of the invention.
Figure 2:
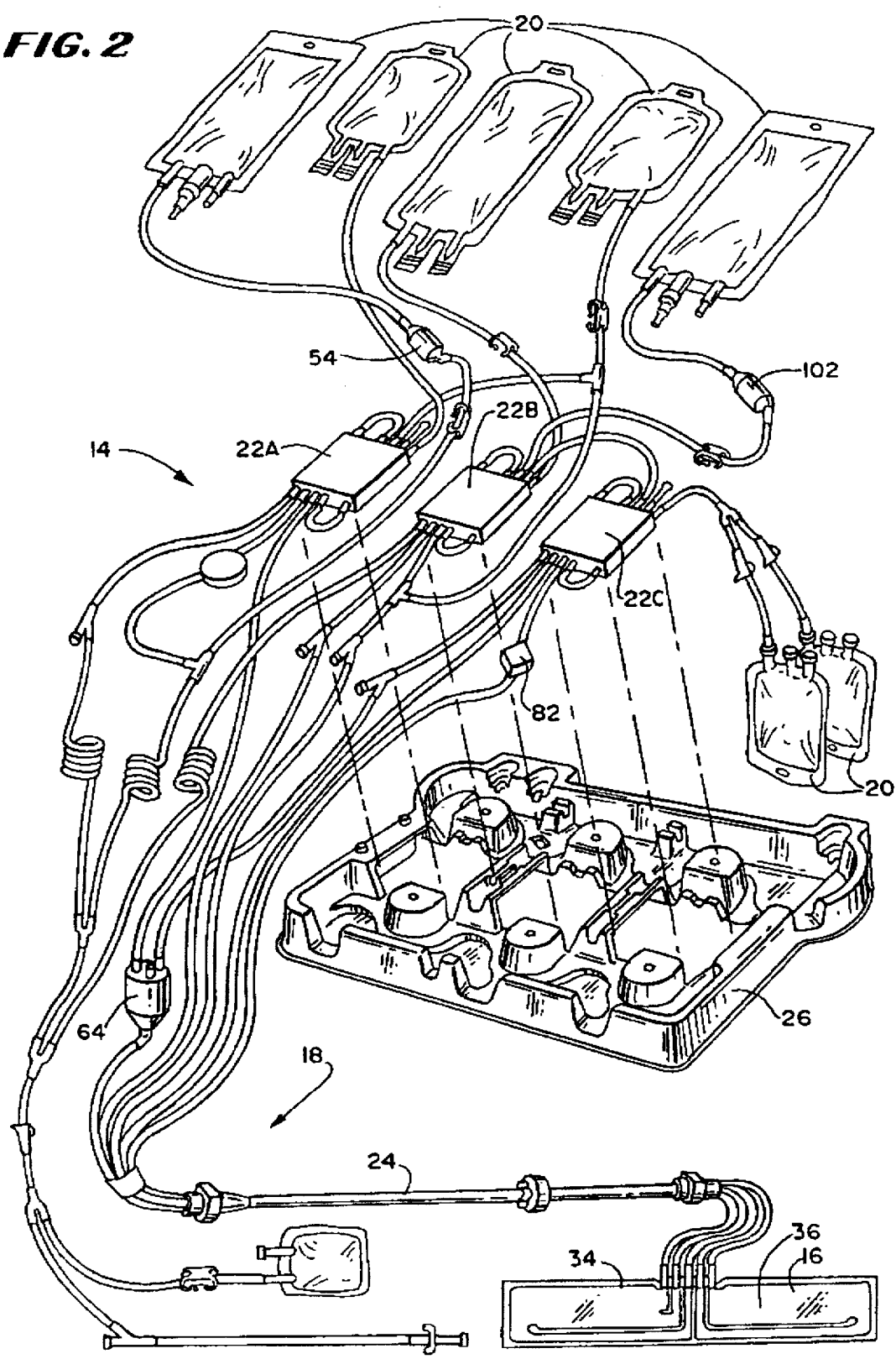
FIG. 2 is an exploded perspective view of a disposable fluid processing assembly usable in association with the centrifuge assembly shown in FIG. 1.
Figure 3:
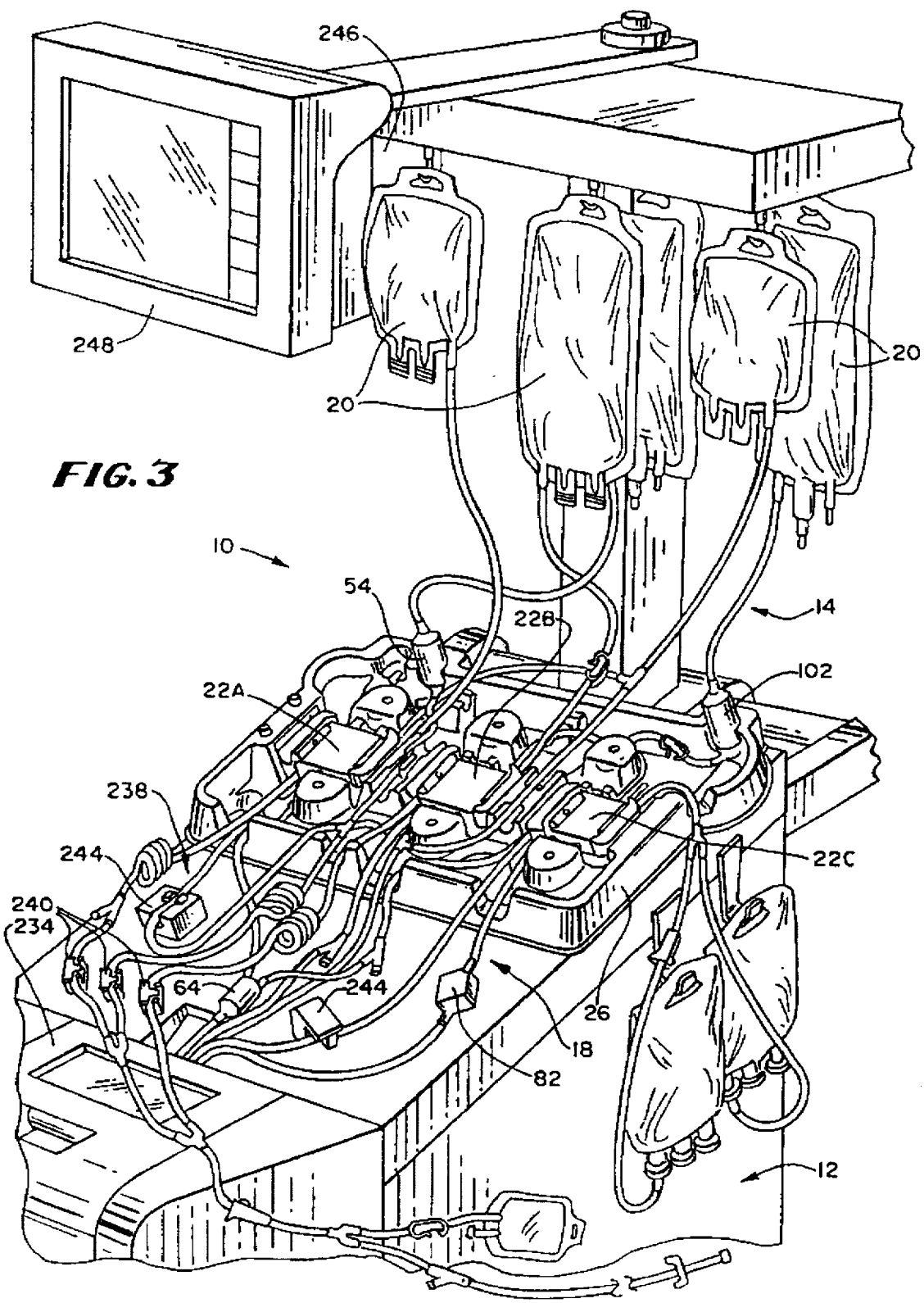
FIG. 3 is a perspective view of a centrifugal processing system that the centrifuge assembly shown in FIG. 1 and the fluid processing assembly shown in FIG. 2 comprise when associated for use.

FIGS. 1 to 3 show a centrifugal processing system 10 that embodies the features of the invention. The system 10 can be used for processing various fluids. The system 10 is particularly well suited for processing whole blood and other suspensions of biological cellular materials. Accordingly, the illustrated embodiment shows the system 10 used for this purpose.

The system 10 includes a centrifuge assembly 12 (see FIG. 1) and a fluid processing assembly 14 (see FIG. 2) used in association with the centrifuge assembly (see FIG. 3).

The centrifuge assembly 12 is intended to be a durable equipment item capable of long term, maintenance free use. The fluid processing assembly 14 is intended to be a single use, disposable item loaded on the centrifuge assembly 12 at time of use (as FIG. 2 shows).

As will be described in greater detail later, the operator removes the fluid processing assembly 14 from the centrifuge assembly 12 upon the completing the procedure and discards it.

I. THE FLUID PROCESSING ASSEMBLY

FIG. 2 shows an exploded view of the disposable processing assembly 14 that is usable in association with the centrifuge assembly.

The assembly 14 includes a processing chamber 16. In use, the centrifuge assembly 12 rotates the processing chamber 16 to centrifugally separate blood components. The construction of the processing chamber 16 can vary.

The processing assembly 14 includes an array of flexible tubing that forms a fluid circuit 18. The fluid circuit 18 conveys liquids to and from the processing chamber 16.

The fluid circuit 18 includes a number of containers 20. In use, the containers 20 fit on hangers on the centrifuge assembly 12 (see FIG. 2) to dispense and receive liquids during processing.

The fluid circuit 18 includes one or more in line cassettes 22. FIG. 2 shows three cassettes, designated 22A; 22B; and 22C.

The cassettes 22A/B/C/serve in association with pump and valve stations on the centrifuge assembly 12 to direct liquid flow among the multiple liquid sources and destinations during a blood processing procedure. The cassettes 22A/B/C centralize the valving and pumping functions to carry out the selected procedure.

A portion of the fluid circuit 18 leading between the cassettes 22 and the processing chamber 16 is bundled together to form an umbilicus 24. The umbilicus 24 links the rotating parts of the processing assembly 14 (principally the processing chamber 16) with the nonrotating, stationary part of the processing assembly 14 (principally the cassettes 22 and containers 20). The umbilicus 24 links the rotating and stationary parts of the processing assembly 14 without using rotating seals.

In the illustrated and preferred embodiment, the fluid circuit 18 preconnects the processing chamber 16, the containers 20, and the cassettes 22. The assembly 14 thereby forms an integral, sterile unit.

In the illustrated and preferred embodiment, the entire processing assembly 14 is packaged for use within an organizer tray 26. The tray 26 holds the processing chamber 16, the containers 20, the cassettes 22, and fluid circuit 18 in an orderly, compact package before use. During use (see FIG. 3), the organizer tray 26 mounts on the centrifuge assembly 12. After processing, the tray 26 receives the processing assembly 14 for disposal.

Specific details of the construction of the organizing tray 26 are not essential to an understanding of the invention and can be found in copending U.S. patent application Ser. No. 08/172,135, filed Dec. 22, 1993 and entitled "Peristaltic Pump Tube Holder with Pump Tube Shield and Cover," which is incorporated herein by reference.

(i) The Fluid Processing Cassette

Each cassette 22A/B/C shares the same construction. FIGS. 4 to 9 show the details of the preferred construction.

Figure 4:
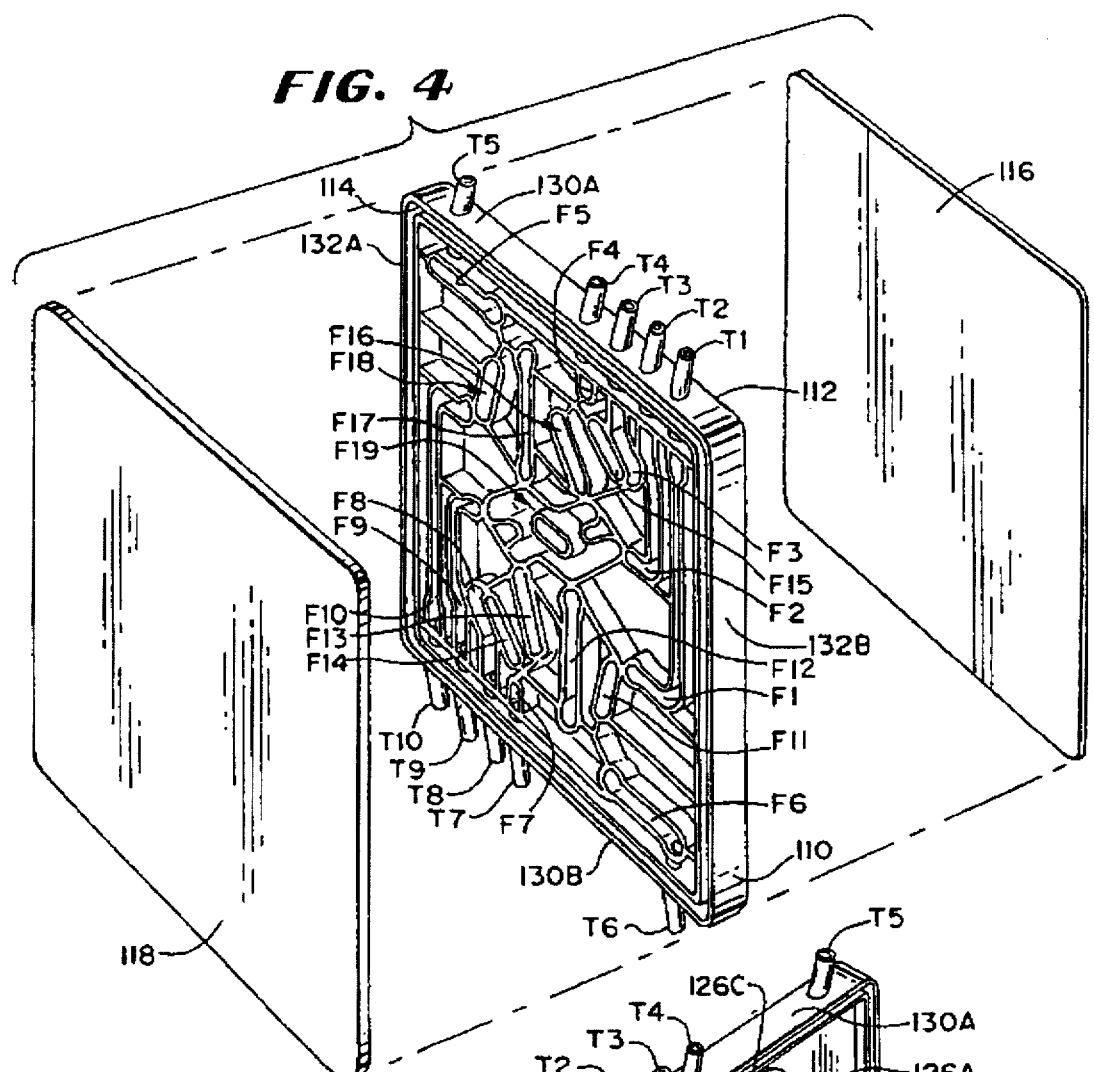
FIG. 4 is an exploded perspective view of a fluid control cassette that the fluid processing assembly shown in FIG. 2 incorporates, looking at the back side of the cassette body.
Figure 5:
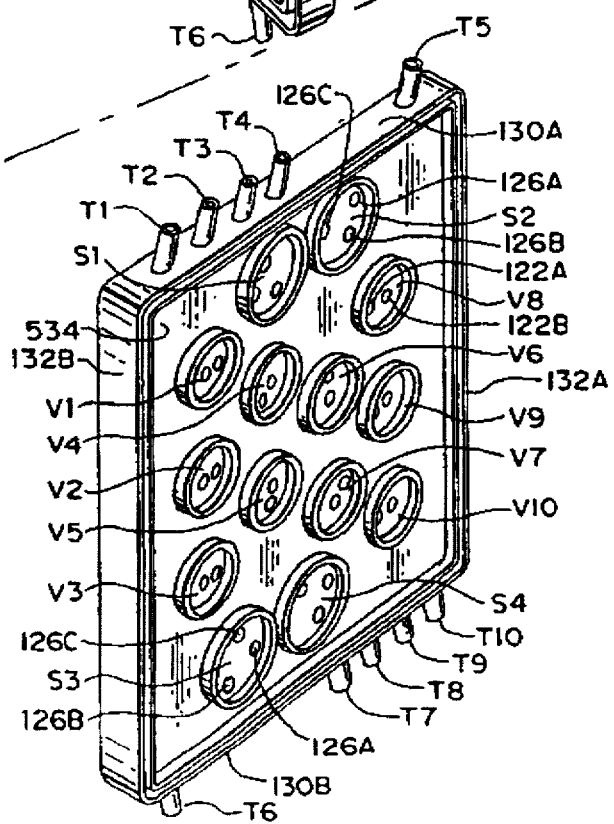
FIG. 5 is a perspective view of the front side of the cassette body shown in FIG. 4.

As FIGS. 4 and 5 best show, the cassette 22 includes an injection molded body 110 that is compartmentalized by an interior wall 534 to present a front side 112 (see FIG. 5) and a back side 114 (see FIG. 4). For the purposes of description, the front side 112 is the side of the cassette 22 that, in use, faces toward the centrifuge assembly 12.

A flexible diaphragm 116 overlies the front side 112 of the cassette 22. A generally rigid back panel 118 overlies the back side 114 of the cassette.

The cassette 22, interior wall 534, and back panel 118 are preferably made of a rigid medical grade plastic material. The diaphragm 116 is preferably made of a flexible sheet of medical grade plastic. The diaphragm 116 and back panel 118 are sealed about their peripheries to the peripheral edges of the front and back sides 112/114 of the cassette 22.

As FIGS. 4 and 5 also best show, the front and back sides 112/114 of the cassette 22 contain preformed cavities.

On the front side 112 of the cassette 22 (see FIG. 5), the cavities form an array of valve stations $V_N$ and an array of pressure sensing stations $S_N$.

On the back side 114 of the cassette 22 (see FIG. 4), the cavities form an array of channels or paths $F_N$ for conveying liquids.

The valve stations $V_N$ communicate with the liquid paths $F_N$ to interconnect them in a predetermined manner. The sensing stations $S_N$ also communicate with the liquid paths $F_N$ to sense pressures in selected regions.

The number and arrangement of the liquid paths $F_N$, the valve stations $V_N$, and the sensing stations $S_N$ can vary. In the illustrated embodiment, the cassette 22 provides nineteen liquid paths F1 to F19, ten valve stations V1 to V10, and four sensing stations S1 to S4.

The valve and sensing stations V1/V10 and S1/S4 resemble shallow wells open on the front cassette side 112 (see FIG. 5). As FIGS. 7 and 8 best show, upstanding edges 120 rise from the interior wall 534 and peripherally surround the stations V1/V10 and S1/S4.

Figure 8:
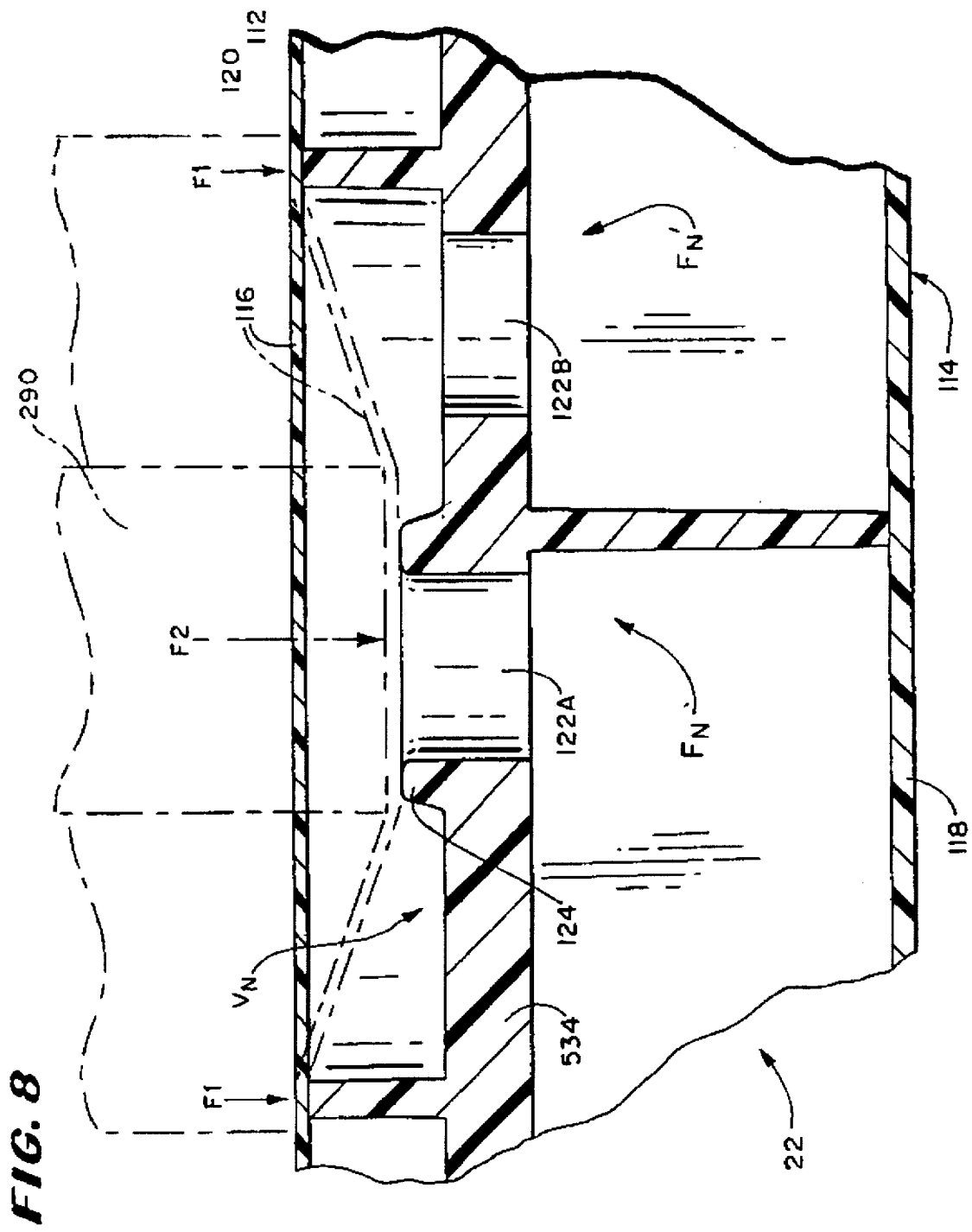
FIG. 8 is an enlarged side section view of a representative valve station located within the cassette body shown in FIG. 4.

The valve stations V1/V10 are closed by the interior wall 534 on the back side 114 of the cassette 22, except that each valve station $V_N$ includes a pair of through holes or ports 122A and 122B in the interior wall 534 (see FIGS. 5 and 8). The ports 122A/B each open into selected different liquid paths $F_N$ and $F_N$, (see FIG. 8) on the back side 114 of the cassette 22. One of the ports 122A is surrounded by a seating ring 124, while the other is not (see FIG. 8).

The sensing stations S1/S4 are likewise closed by the interior wall 534 on the back side 114 of the cassette 22, except that each sensing station $V_N$ includes three through holes or ports 126A/B/C in the interior wall 534 (see FIG. 5). The ports 126A/B/C open into selected liquid paths $F_N$ on the back side 114 of the cassette 24. These ports 126 A/B/C channel liquid flow among the selected liquid paths $F_N$ through the associated sensing station.

Figure 7:
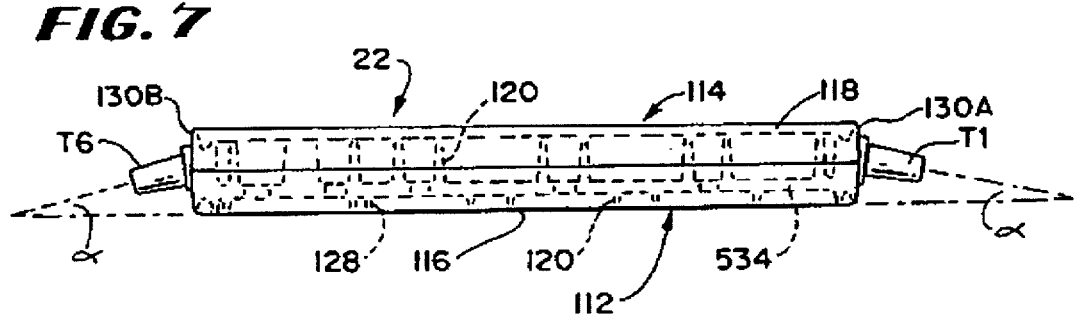
FIG. 7 is a side view of the cassette body, taken generally along line 7—7 in FIG. 6.

As FIGS. 7 and 8 best show, the flexible diaphragm 116 overlying the front side 112 of the cassette 22 is sealed by ultrasonic welding to the upstanding peripheral edges 120 of the valve and sensing stations V1/V10 and S1/S4. This isolates the valve stations V1/V10 and sensing stations S1/S4 from each other and the rest of the system.

Alternatively, the flexible diaphragm 116 can be seated against the upstanding edges 120 by an external positive force applied by the centrifuge assembly 12 against the diaphragm 116 (as shown by the F1-arrows in FIG. 8). The positive force F1, like the ultrasonic weld, peripherally seals the valve and sensing stations V1/V10 and S1/S10.

As shown in phantom lines in FIG. 8, the localized application of additional positive force upon the intermediate region of the diaphragm 116 overlying a valve station V1/V10 (as shown by the F2-arrow in FIG. 7) serves to flex the diaphragm 116 into the valve station. The diaphragm 116 seats against the ring 124 (as shown by phantom lines in FIG. 8) to seal the associated valve port 122A. This closes the valve station to liquid flow.

Upon removal of the force F2, fluid pressure within the valve station and/or the plastic memory of the diaphragm 116 itself unseats the diaphragm 116 from the valve ring 124, opening the valve station to liquid flow.

Preferably, the diameter and depth of the valve stations are selected so that the flexing required to seat the diaphragm 116 does not exceed the elastic limits of the diaphragm material. In this way, the plastic memory of the plastic material alone is sufficient to unseat the diaphragm 116 in the absence of the force F2.

As will be described in greater detail later, in use, the centrifuge assembly 12 selectively applies localized positive force F2 to the diaphragm 116 for closing the valve ports 122A.

As FIGS. 7 and 8 best show, upstanding edges 128 rise from the interior wall 534 and peripherally surround the channels F1/F19, which are open on the back side 114 of the cassette 22.

Figure 6:
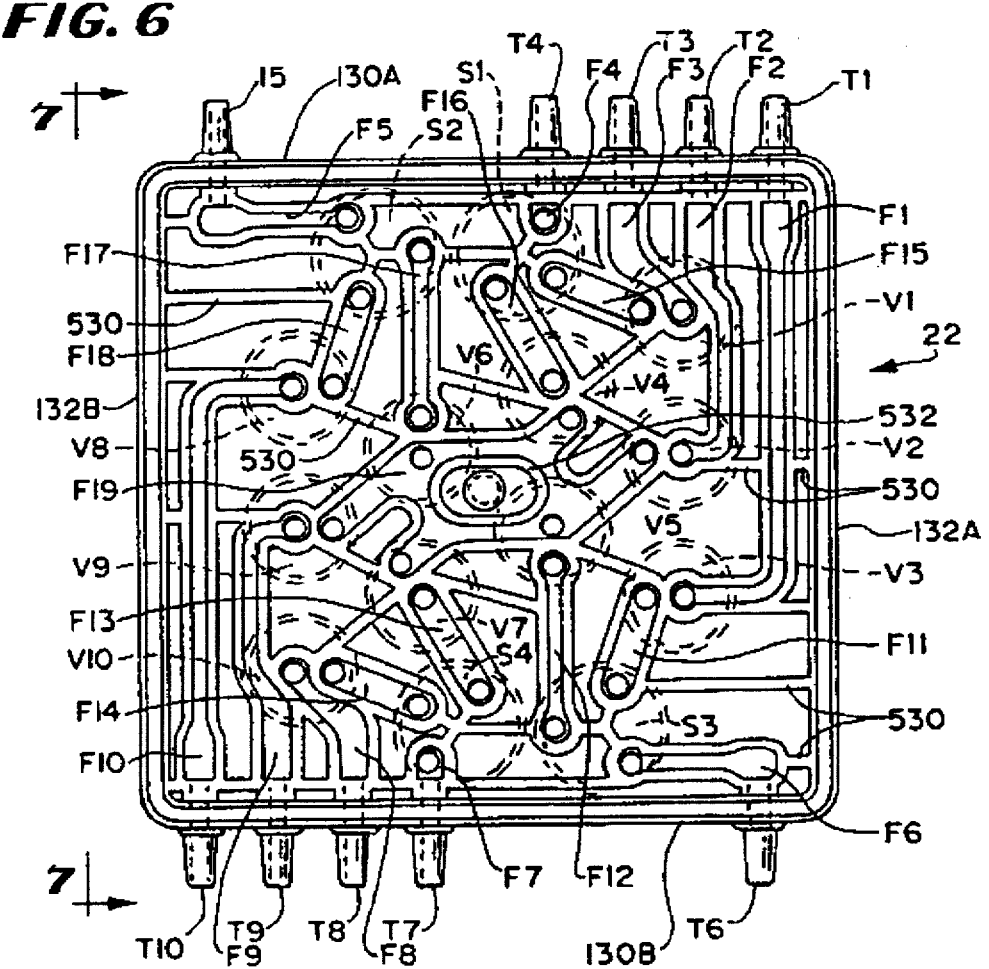
FIG. 6 is a plan view of the fluid circuits and interconnecting valve and sensing stations that the cassette body shown in FIG. 4 carries, looking at the back side of the cassette body.

The liquid paths F1/F19 are closed by the interior wall 534 on the front side 112 of the cassette 22, except for the ports 122A/B of the valve stations V1/V10 and the ports 126A/B/C of the sensing stations S1/S4 (see FIG. 6).

The rigid panel 118 overlying the back side 114 of the cassette 22 is sealed by ultrasonic welding to the upstanding peripheral edges 128, sealing the liquid paths F1/F19 from each other and the rest of the system 10.

As FIG. 6 best shows, ten premolded tube connectors T1 to T10 extend out along opposite side edges 130A/B of the cassette 22. The tube connectors are arranged five on one side edge 130A (T1 to T5) and five on the other side edge 130B (T6 to T10). The other side edges 132A/B of the cassette 22 are free of tube connectors. This ordered orientation of the tube connectors T1/T10 along only two side edges 130A/B of the cassette 22 provides a centralized, compact unit for mounted on the centrifuge assembly 12 (as FIG. 3 shows).

As FIG. 6 shows, along one side edge 130A, the first through fifth tube connectors T1 to T5 communicate with interior liquid paths F1 to F5, respectively. Along the other side edge 130B, the sixth through tenth tube connectors T6 to T10 communicate with interior liquid paths F6 to F10, respectively. These liquid paths F1 to F10 constitute the primary liquid paths of the cassette 22, through which liquid enters or exits the cassette 22.

The remaining interior liquid paths F11 to F19 of the cassette 22 constitute branch paths that link the primary liquid paths F1 to F10 to each other through the valve stations V1 to V10 and sensing stations S1/S4.

More particularly, valve station V3 controls liquid flow between primary liquid path F1 and branch fluid path F11. Valve station V2 controls liquid flow between primary liquid path F2 and branch path F19. Valve station V1 controls liquid flow between primary liquid path F3 and branch path F15. Sensing station S1 links primary flow path F4 with branch paths F15 and F16. Sensing station S2 links primary flow path F5 with branch paths F17 and F18.

Similarly, valve station V10 controls liquid flow between primary liquid path F8 and branch fluid path F14. Valve station V9 controls liquid flow between primary liquid path F9 and branch path F19. Valve station V8 controls liquid flow between primary liquid path F10 and branch path F18. Sensing station S3 links primary flow path F6 with branch paths F11 and F12. Sensing station S4 links primary flow path F7 with branch paths F13 and F14.

The branch paths F16, F12, F17, and F13 communicate with branch path F19 through valve stations V4, V5, V6, and V7, respectively.

In this arrangement, branch path F19 serves as a central hub for conveying liquid between the primary fluid paths F1 to F5 on one side 130A of the cassette 22 and the primary fluid paths F6 to F10 on the other side 130B of the cassette 22. The branch paths F16 and F17 feed the central hub F19 from the side 130A of the cassette 22, while the branch paths F12 and F13 feed the central hub F19 from the other side 130B of the cassette 22.

In the illustrated and preferred embodiment (see FIGS. 6 and 9), an upstanding, generally elliptical ridge 532 occupies the mid-portion of the central hub F19. The ridge 532 helps to channel fluid within the hub F19 to the respective branch paths communicating with it. The ridge 532 also reduces the overall fluid volume of the hub F19 to facilitate liquid conveyance within it.

Figure 9:
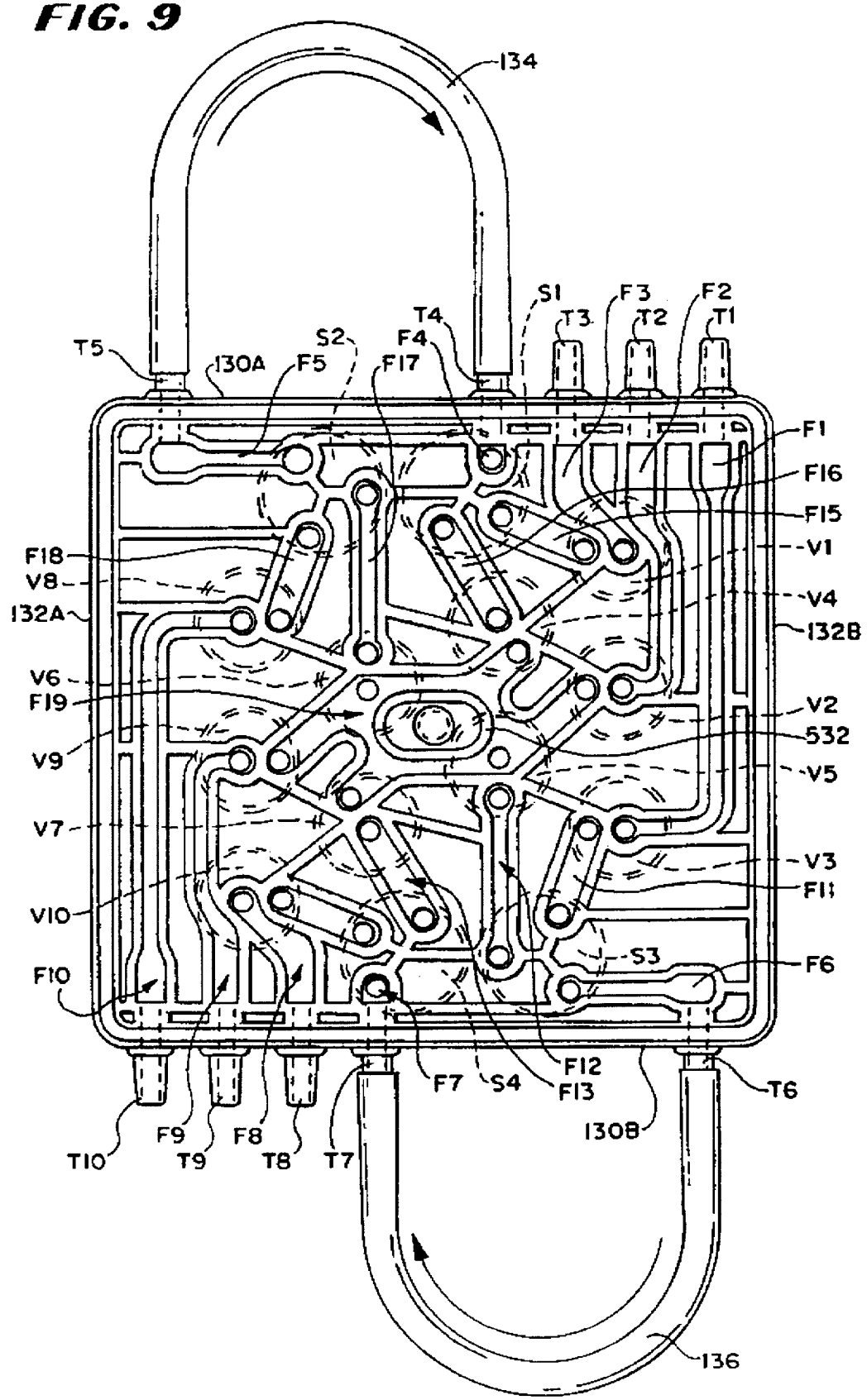
FIG. 9 is a plan view, taken on the back side of the cassette body, of the cassette shown in FIG. 4, with the tubing loops attached and ready for use.

As FIG. 9 shows, external tubing loop 134 connects tube connector T4 with tube connector T5 on the side edge 130A. Likewise, external tubing loop 136 connections tube connector T7 with tube connector T6 on the other side edge 130B. In use, the tube loops 134 and 136 engage peristaltic pump rotors on the centrifuge assembly 12 to convey liquid into the cassette 22 and from the cassette 22.

As FIG. 7 shows, the tube connectors T1/T2 and T9/T10 extend from their respective side edges 130A/B in a sloping direction toward the front side 112 of the cassette 22. In the illustrated and preferred embodiment, the angle α that the sloped tube connector T1/T2 and T9/T10 make with the plane of the front side 112 of the cassette 22 is about 10 degrees. The angled relationship of the tube connectors T1/T2 and T9/T10 facilitates loading the associated tubing loops 134 and 136 on the peristaltic pump rotors.

The remaining tube connectors T3 to T8 on the cassette 22 are connected with the flexible tubing of the fluid circuit 18.

More specific details of the construction of the cassette 22 are not essential to an understanding of the invention and can be found in copending U.S. patent application Ser. No. 08/173,517, filed Dec. 22, 1993 and entitled "Peristaltic Pump Tube Cassette for Blood Processing System and the Like," which is incorporated herein by reference.

(ii) Processing Assemblies for Platelet Collection

Figure 11:
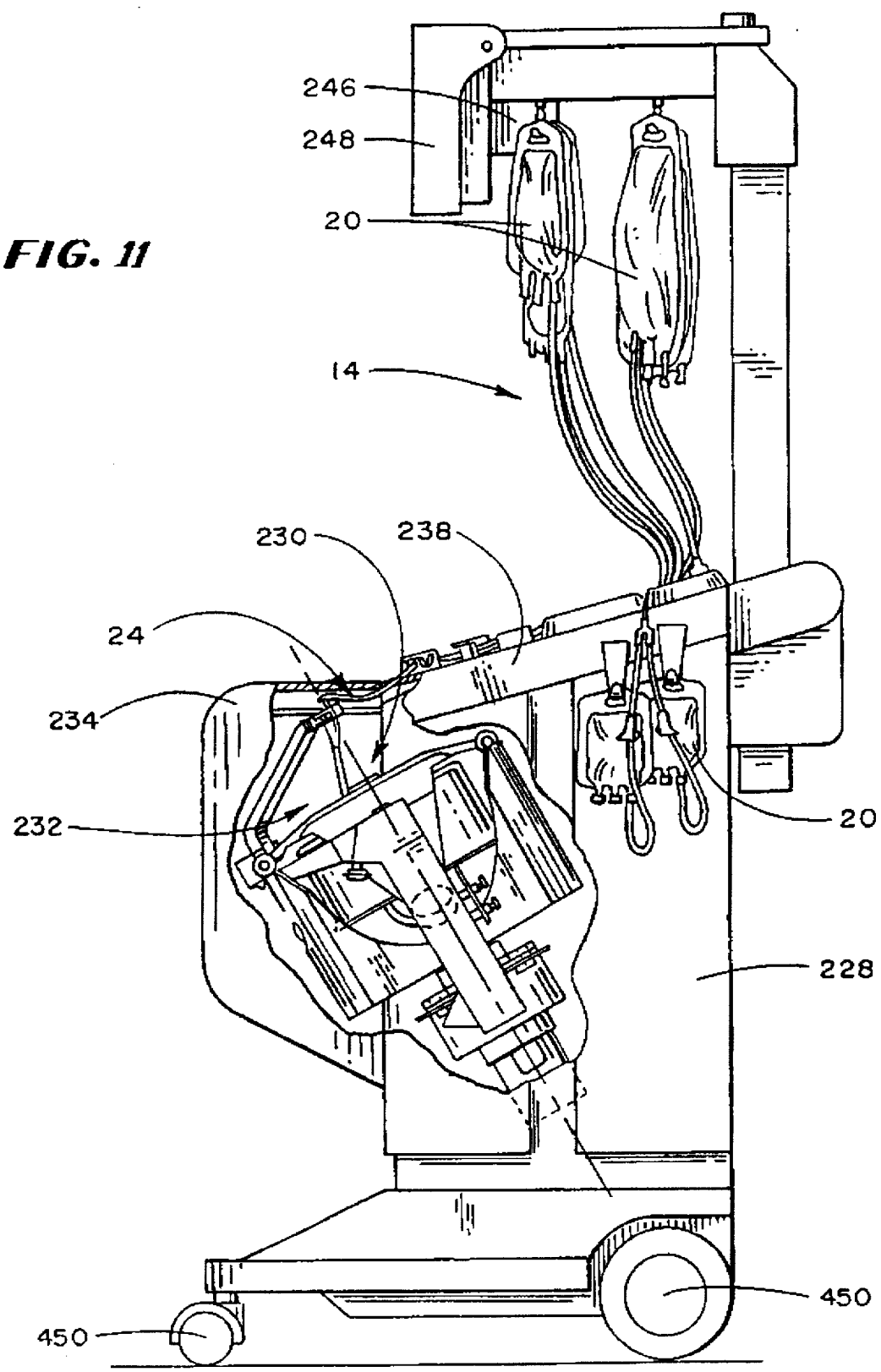
FIG. 11 is a side elevation view of the centrifuge assembly shown in FIG. 1, with the fluid processing assembly mounted for use, and with portions broken away to show the compartment that houses the associated centrifuge.

The processing assembly 14 as just described can be configured to accomplish diverse types of processing techniques. FIG. 11 shows a representative a single needle platelet collection system 28 (FIGS. 2 and 3 also show the single needle system 28 in association with the tray 26 and centrifuge assembly 12).

The system 28 includes the processing chamber 16 and containers 20 interconnected by the fluid circuit 18 carried by the organizer tray 26. The fluid circuit 18 for the system 28 includes the three centralized pumping and valving cassettes, identified as 22A; 22B; and 22C. The umbilicus 24 links the rotating and non-rotating components in each system 28 and 30.

The processing chamber 16 can be variously constructed. For example, it can be constructed like the double bag processing chambers shown in Cullis et al. U.S. Pat. No. 4,146,172.

In the illustrated and preferred embodiment, the processing chamber 16 in each system 28 and 30 is formed as an elongated flexible tube made of a flexible, biocompatible plastic material such as plasticized medical grade polyvinyl chloride. The chamber 16 includes a first stage compartment 34 and a second stage compartment 36.

The first stage compartment 34 receives whole blood (WB). When subjected to centrifugal forces, the first stage compartment 34 separates the WB into red blood cells (RBC) and platelet rich plasma (PRP).

The second stage compartment 36 receives PRP from the first stage compartment 32. When subjected to centrifugal forces, the second stage compartment 36 separates the PRP into concentrated platelets (PC) and platelet-poor plasma (PPP).

Specific details of the construction of the processing chamber 16 are not essential to an understanding of the invention and can be found in copending U.S. patent application Ser. No. 07/965,074, filed Oct. 22, 1992 and entitled "Enhanced Yield Blood Processing Systems and Methods Establishing Vortex Flow Conditions," which is incorporated herein by reference.

The fluid circuit 18 includes five tubing branches 38/40/42/44/46 that communicate directly with the processing chamber 16. Three tubing branches 38/40/42 serve the first stage compartment 34. Two tubing branches 44/46 serve the second stage compartment 36.

The tubing branch 40 carries WB into the first stage compartment 34 for processing. The tubing branch 38 carries separated PRP from the first stage compartment 34. The tubing branch third port 42 carries separated RBC from the first stage compartment 34.

The tubing branch 46 carries PRP separated in the first compartment 34 into the second compartment 36 for further processing. The tubing branch 44 carries separated PPP from the second stage compartment 36. The separated PC remains in the second stage compartment 36 for later resuspension and collection.

The cassettes 22A/B/C serve to segregate the flow paths of various categories of fluids and blood components from each other during processing.

The cassette 22A principally handles the flow of fluids containing red blood cells, either as WB or as RBC. The cassette 22B principally handles the flow of cellular-free fluids, either as PPP or anticoagulant. The cassette 22C principally handles the flow of fluids containing platelets, either as PRP or PC.

The fluid circuit 18 for the single needle system 28 (see FIG. 10) includes a tubing branch 32 that carries a phlebotomy needle 48 for drawing WB from a donor. A tubing branch 33 joins the tubing branch 32 and leads to the cassette 22A. A tubing branch 100 carries an anticoagulant solution from a container 98 into the tubing branch cassette 22B (via a drip chamber 102). The anticoagulant flows from cassette 22B through tubing branch 92 for addition to the WB before processing. A tubing branch 56 leads from the cassette 22A to convey anti-coagulated WB to a reservoir container 58.

Another tubing branch 60 leads from the cassette 22A to convey anti-coagulated WB into the umbilicus 24 via a drip chamber 64 and tubing branch 62. The umbilicus 24 joins tubing branch 40, which carries the anti-coagulated WB into the first stage chamber 34 for separation into RBC and PRP.

The tubing branch 42 carries the separated RBC from the first stage chamber 34 through the umbilicus 24. The umbilicus 24 joins the tubing branches 64, 66, and 68, which lead to a reservoir container 70 for RBC.

A tubing branch 72 joins tubing branch 68 to carry RBC from the reservoir container 70 to the cassette 22A. The tubing branch 74 leads from the cassette 22A to carry RBC to the tubing branch 32, which leads to the phlebotomy needle 48.

The cassette 22A thereby directs the flow of anti-coagulated WB from the donor into the first stage compartment 34. The cassette 22A also directs the flow of separated RBC from the first stage compartment 34 back to the donor.

These flows are sequenced to proceed in two cycles. One cycle draws WB from the donor, while the other returns RBC to the donor.

In the draw cycle, the single needle system 28 collects through the cassette 22A a predetermined volume of anti-coagulated WB in the reservoir container 58 (through tubing branches 32/33/56), while conveying the rest of the anti-coagulated WB continuously to the first stage compartment 34 for separation (through tubing branches 32/33/60/62/40). During the draw cycle, the system 28 also continuously collects the separated RBC in the reservoir container 70 (through tubing branches 42/64/66/68).

In the return cycle, the system 28 continuously conveys through the cassette 22A anti-coagulated WB from the reservoir container 58 into the first stage compartment 34 for separation (through tubing branches 56/60/62/40). At the same time, the system 28 returns through the cassette 22A the RBC collected in the reservoir container 70 to the donor (through tubing branches 68/72/74/32) as well as those RBC being then separated in the first stage compartment 34 (via tubing branches 64 and 66, joining tubing branch 68).

This two cycle sequence through the cassette 22A assures that anti-coagulated WB is continuously conveyed to the first stage compartment for separation, either from the donor (during the draw cycle) or from the WB reservoir container 58 (during the return cycle).

The tubing branch 86 carries separated PRP from the first stage compartment 34 through the umbilicus 24 to the cassette 22C.

A portion of the PRP is conveyed from the cassette 22C through tubing branch 80. Tubing branch 80 leads to the umbilicus 24, which joins tubing branch 46, which takes the PRP into the second stage compartment 36 for further separation into PPP and PC.

In the illustrated and preferred embodiment, the tubing branch 80 carries an in line filter 82. The filter 82 removes leukocytes from the PRP before it enters the second stage compartment 36 for separation.

Another portion of the PRP is conveyed from the cassette 22C through tubing branch 84 to the drip chamber 64, where it mixes with the anti-coagulated WB being conveyed into the first stage compartment 34. This recirculation of PRP improves the yield of platelets.

Further details of the in line filtration and recirculation of PRP are not essential to an understanding of the invention and are disclosed in copending patent application Ser. No. 08/097,454, filed Jul. 26, 1993, and entitled "Systems and Methods for Reducing the Number of Leukocytes in Cellular Products Like Platelets Harvested for Therapeutic Purposes."

The tubing branch 44 carries PPP from the second stage compartment 36 through the umbilicus 24 and to tubing branch 76, which leads to the cassette 22B. Tubing branch 88 carries the PPP from the cassette 22B to a reservoir container 90.

During processing, a portion of the PPP collected in the reservoir container 90 is returned to the donor with the RBC during the return cycle. This portion of PPP is conveyed from the reservoir container 90 through tubing branch 66 via the cassette 22B to tubing branch 72, which joins the tubing branch 33 via cassette 22A. At the same time, PPP then being separated in the second stage compartment 36 is returned to the donor through tubing branches 85 and 76 to the tubing branch 66 via the cassette 22B.

Another portion of the PPP collected in the reservoir container 90 is used to resuspend PC in the second stage compartment 36 after separation ends. This portion of PPP is conveyed from the reservoir container 90 through tubing branch 88 via the cassette 22B, back through tubing branch 76, the umbilicus 24, and tubing branch 44 into the second stage compartment 36. There, the PPP resuspends PC accumulated in the compartment 36. The tubing branch 46 conveys resuspended PC from the compartment 36, through the umbilicus 24 to tubing branch 86, which joins the cassette 22C. Tubing branch 94 conveys resuspended PC from the cassette 22C to collection containers 96.

Other portions of the PPP collected in the reservoir container 90 can also be used for additional processing purposes. For example, the PPP (which carries most of the anticoagulant added during processing) can serve as an anti-coagulated "keep open" fluid, to keep the phlebotomy needle 48 open during lulls in processing. The PPP can also be used as a "final flush" fluid, to purge the tubing branches after processing.

The PPP remaining in the reservoir container 90 after processing can be stored for therapeutic purposes.

Further details of the collection and use of PPP as a processing aid are not essential to an understanding of the invention and are disclosed in copending patent applications Ser. No. 08/097,967, filed Jul. 26, 1993 and entitled "Systems and Methods for On Line Collection of Cellular Blood Components that Assure Donor Comfort" and Ser. No. 08/097,293, filed Jul. 26, 1993, and entitled "Systems and Methods for On Line Collecting and Resuspending Cellular Blood Products Like Platelet Concentrate."

Container 50 holds a saline priming solution, which is used to purge air from the system 28 before processing. Tubing branch 52 carries the saline from the container 50 (via the drip chamber 54) to cassette 22A. The saline is conveyed from the cassette 22A into the processing chamber 16 via tubing branches 60 and 62, and from there to the rest of the system 28 along the tubing branches already described.

II. THE CENTRIFUGE ASSEMBLY

The centrifuge assembly 12 (see FIGS. 1 and 11) carries the operating elements essential for a diverse number of blood processing procedures under the direction of an onboard controller.

As FIGS. 1 and 11 show, the centrifuge assembly 12 is housed with a wheeled cabinet 228, which the user can easily move from place to place. It should be appreciated that, due to its compact form, the centrifuge assembly 12 also could be made and operated as a tabletop unit.

Figure 12:
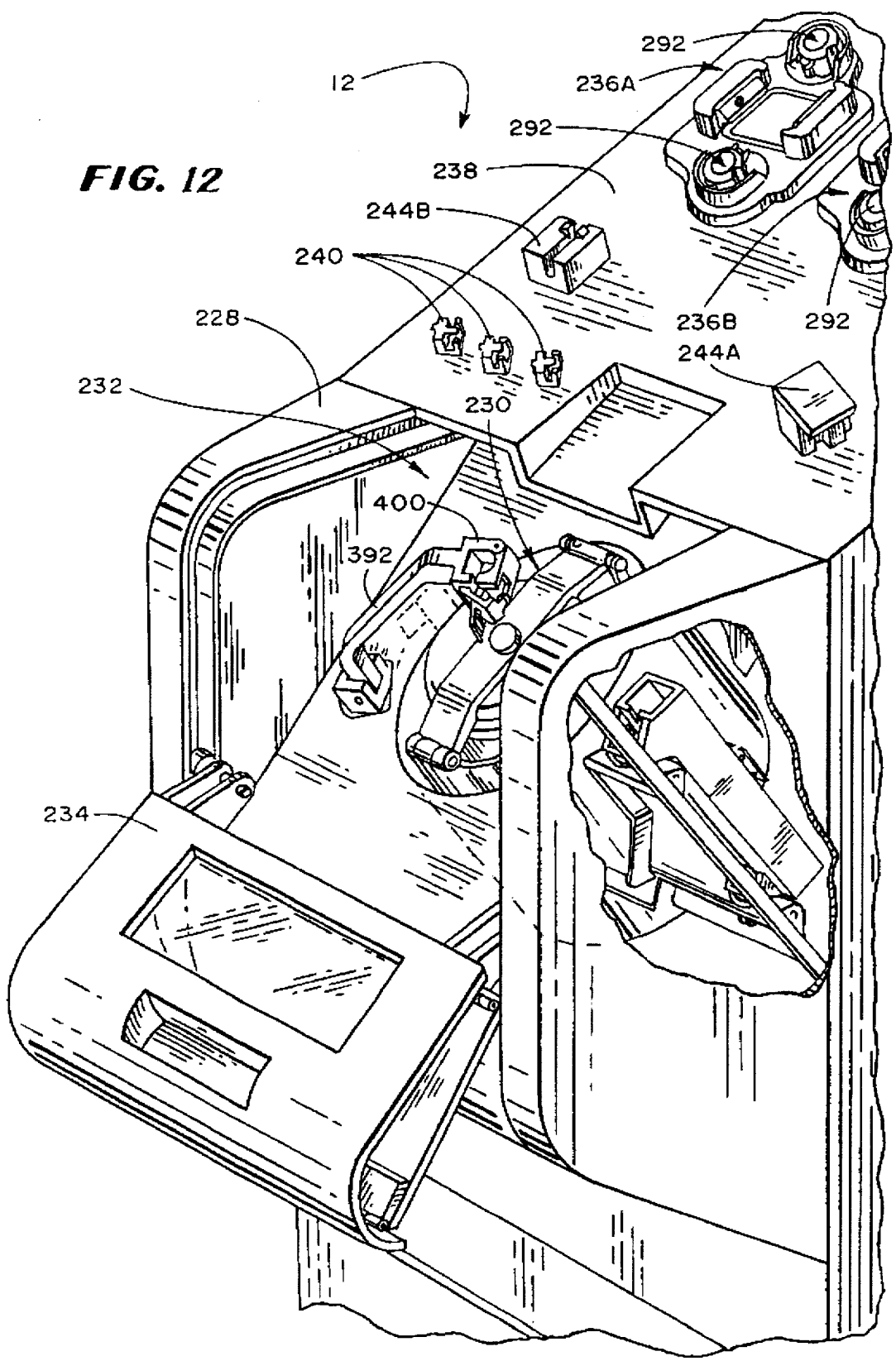
FIG. 12 is a perspective view of the compartment with the door opened to gain access to the centrifuge.

The centrifuge assembly 12 includes a centrifuge 230 (see FIG. 11 mounted for rotation inside a compartment 232 of the cabinet 228. The compartment 232 has a fold-open door 234, which the user opens (see FIG. 12) to gain access to the centrifuge 230 to load and unload the processing chamber 16 of the fluid circuit 18.

Specific details of the construction of the centrifuge 230 are not essential to an understanding of the invention and can be found in copending U.S. patent application Ser. No. 08/176,425, filed Dec. 22, 1993 and entitled "Centrifuge with Pivot Out, Easy Load Processing Chamber," which is incorporated herein by reference.

Figure 13:
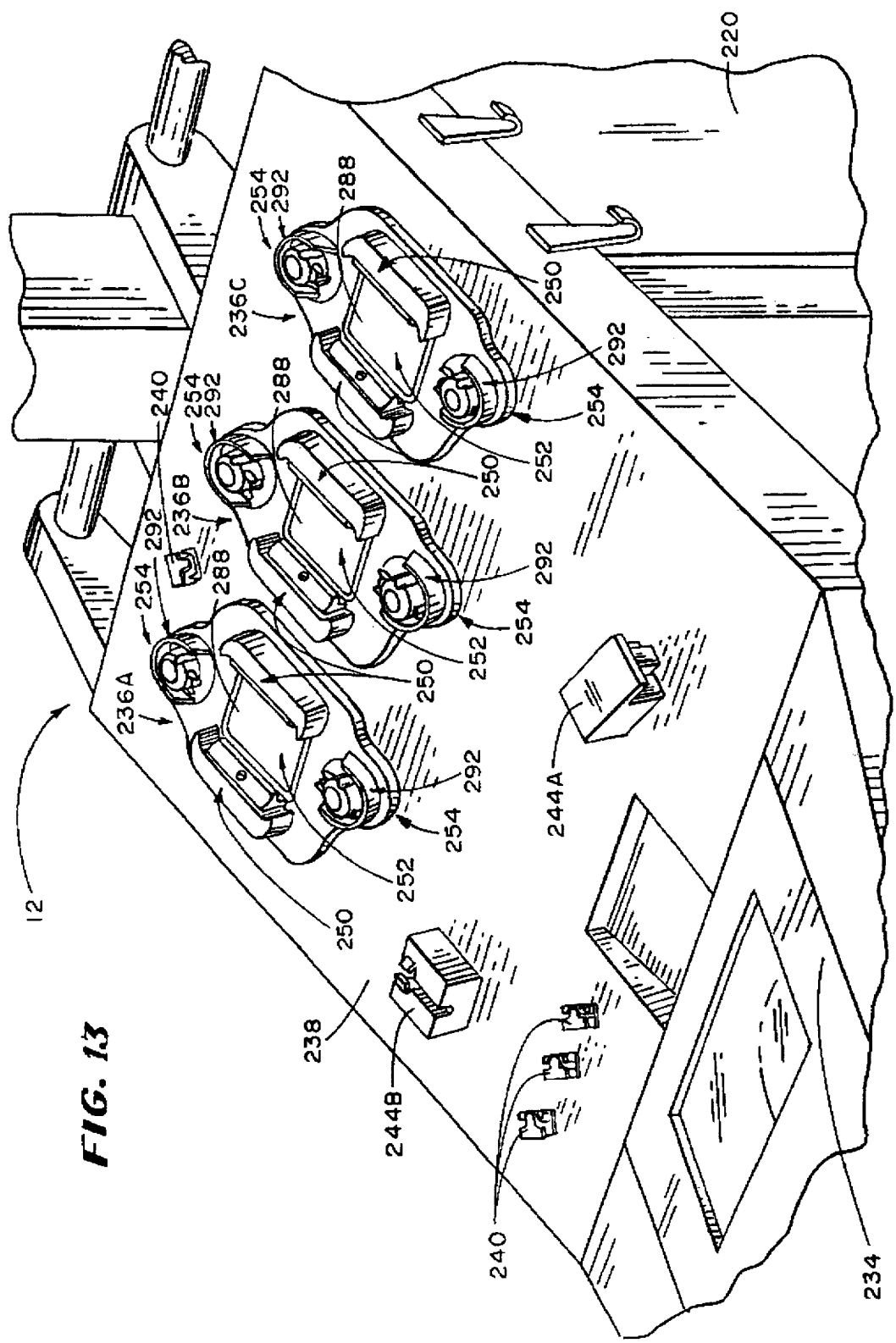
FIG. 13 is a perspective view of the cassette holding stations located on the sloped front panel of the centrifuge assembly, just above the associated centrifuge shown in FIG. 11.

The centrifuge assembly 12 also includes three cassette control stations 236 A/B/C (see FIG. 13), one for each cassette 22 A/B/C. The cassette control stations 236 A/B/C are located side by side on a sloped outside panel 238 of the cabinet 228. The outside panel 238 also carries the shut-off clamps 240, hemolysis sensor 244A, and air detector 244B associated with the centrifuge assembly 12 (see FIG. 13).

The centrifuge assembly 12 includes a processing controller 246. The controller 246 governs the operation of the centrifuge assembly 12. The processing controller 246 preferably includes an integrated input/output terminal 248 (also seen on FIG. 1), which receives and display information relating to the processing procedure.

(i) The Cassette Control Stations

Figure 15:
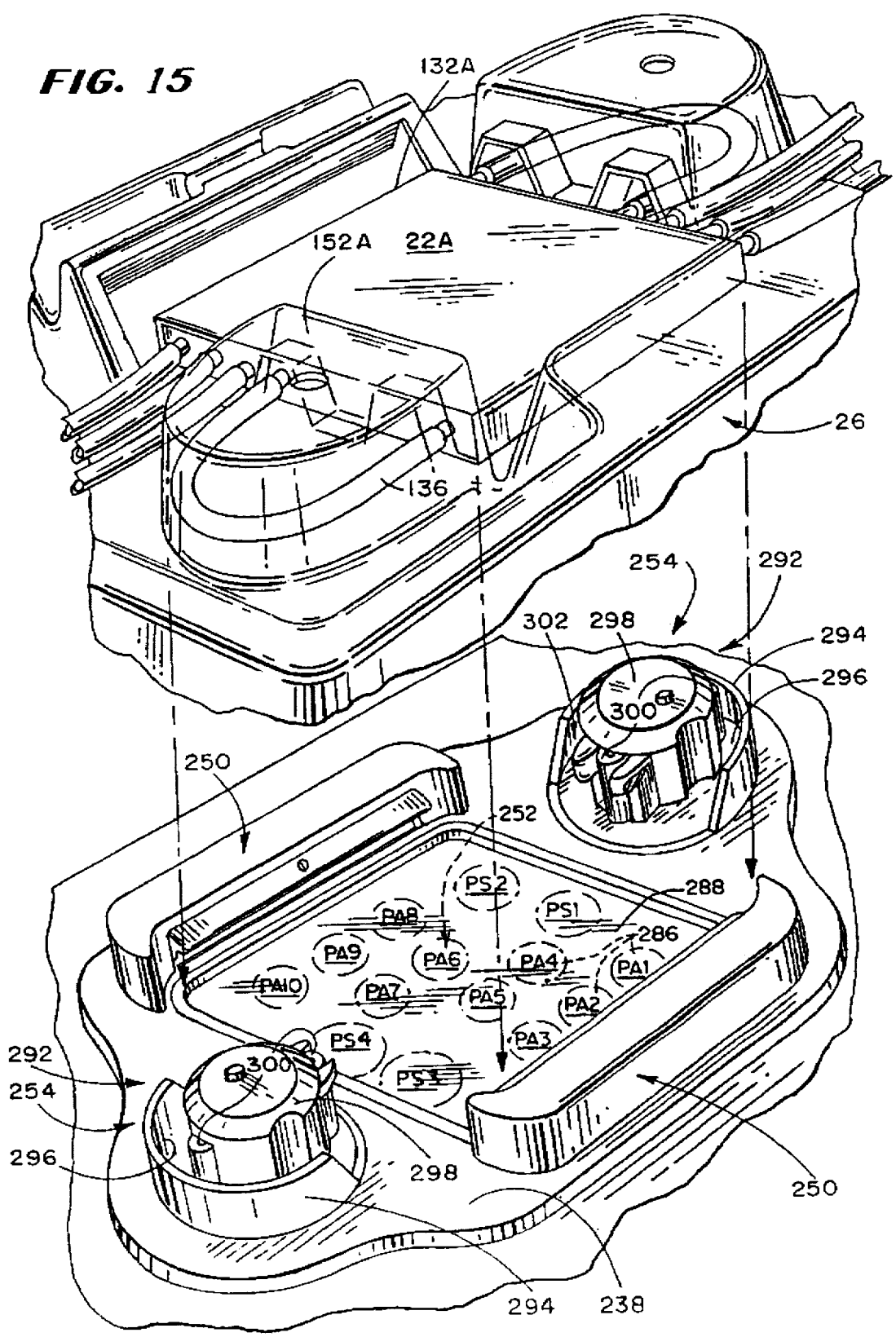
FIG. 15 is a perspective view of a cassette, carried within the tray, positioned for placement on the cassette holding station shown in FIG. 14.

In use, each control station 236A/B/C holds one cassettes 22A/B/C (see FIG. 15). The control station are all constructed alike, so the details of only one station 236A will be provided. In use, the station holds the cassette 22A.

The control station 236A (see FIGS. 14 and 15) includes a cassette holder 250. The holder 250 receives and grips the cassette 22A along two opposed sides 132A and B in the desired operating position on the control station 236A (as FIG. 3 shows).

The holder 250 urges the diaphragm 116 on the front cassette side 112 into intimate contact with a valve module 252 on the control station 236 A. The valve module 252 acts in concert with the valve stations V1/V10 and sensing stations S1/S2/S3/S4 in the cassette 22A.

Specific details of the construction of the holder 250 are not essential to an understanding of the invention and can be found in copending U.S. patent application Ser. No. 08/172, 654, filed Dec. 22, 1993 and entitled "Peristaltic Pump Module Having Jaws for Gripping a Peristaltic Pump Tube Cassette," which is incorporated herein by reference.

The control station also includes a peristaltic pump module 254. When the cassette 22A is gripped by the holder 250, the tubing loops 134 and 136 make operative engagement with the pump module 254.

The controller 246 governs the operation of holder 250 on each control station 236A/B/C to grip the cassettes 22A/B/C upon receipt of a preselected command signal. The controller 246 then proceeds to govern the operation of the valve module 252 and pump module 254 on each control station 236A/B/C to convey liquids through the cassettes 22A/B/C to achieve the processing objectives of the system 10.

(ii) The Cassette Valve Module

Referring back to FIG. 14, the valve module 252 on each control station 236A/B/C contains an array of valve assemblies 286 located between the gripping elements 256. The force F1 that the gripping elements 256 exert (see FIG. 8), hold the diaphragm 116 of the cassette 22A in intimate contact against the valve assemblies 286.

Figure 14:
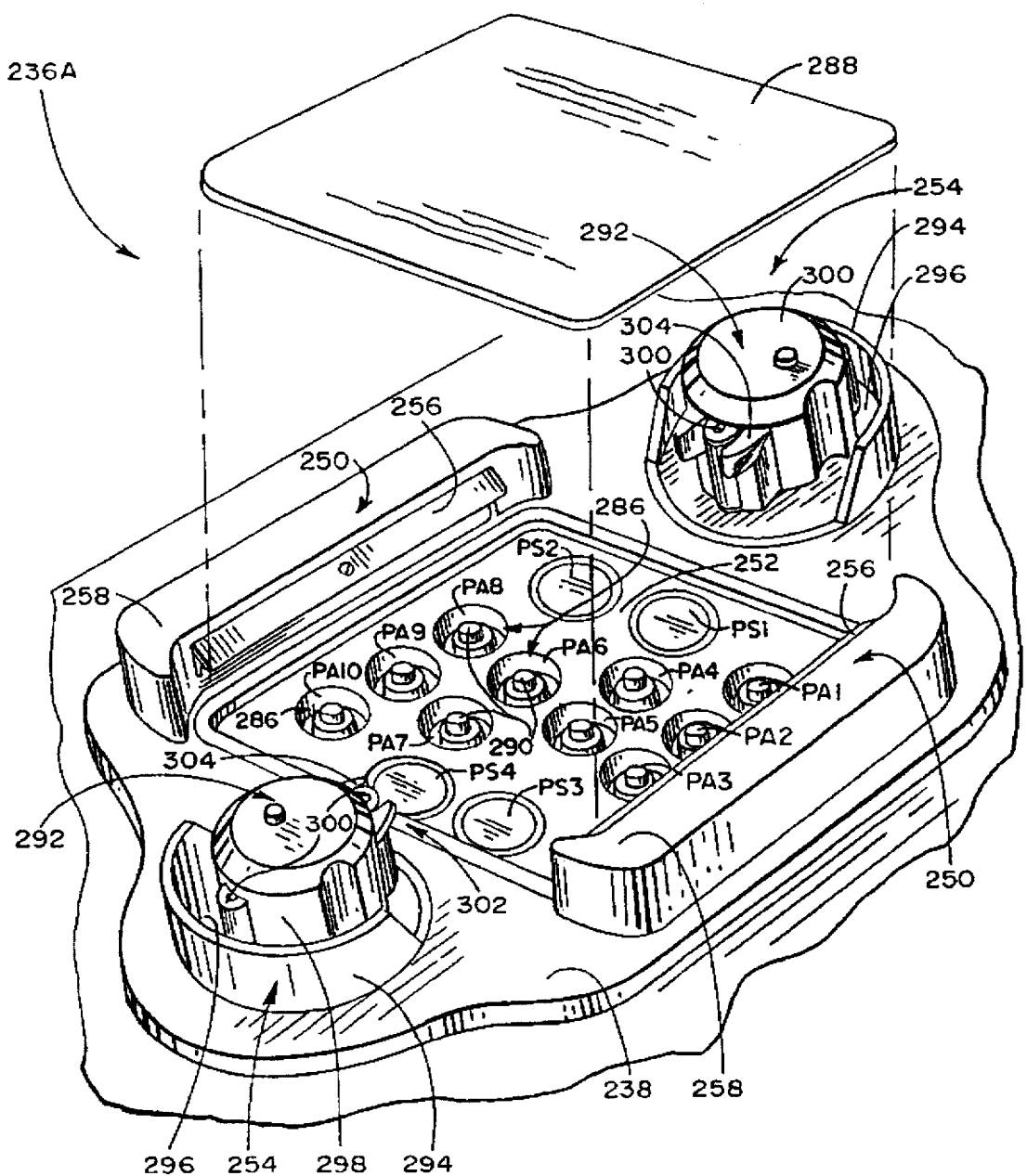
FIG. 14 is a perspective view of the pump and valve modules on one cassette holding station, with the splash guard lifted to show the associated valve assemblies and pressure sensors.

In the illustrated and preferred embodiment (as FIG. 14 shows), a thin elastomeric membrane 288 is stretched across the valve assembly 286, serving as a splash guard. The splash guard membrane 288 keeps liquids and dust out of the valve assembly 286. The splash guard membrane 288 can be periodically wiped clean when cassettes are exchanged.

The valve assembly 286 includes ten valve actuating pistons PA1 to PA10 and four pressure sensing transducers PS1 to PS4. The valve actuators PA1 to PA10 and the pressure sensing transducers PS1 to PS4 are mutually arranged to form a mirror image of the valve stations V1 to V10 and sensing stations S1 to S4 on the front side 112 of the cassette 22A.

When the cassette 22A is gripped by the elements 256, the valve actuators PA1 to PA10 align with the cassette valve stations V1 to V10. At the same time, the pressure sensing transducers PS1 to PS4 mutually align with the cassette sensing stations S1 to S4.

Each valve actuator PA1 to PA10 comprises an electrically actuated solenoid piston 290. Each piston 290 is independently movable between an extended position and a retracted position.

When in its extended position, the piston 290 presses against the region of the diaphragm 116 that overlies the associated valve station V1/V10 (exerting the force F2 shown in FIG. 8). In this position, the piston 290 flexes the diaphragm 116 into the associated valve station to seat the diaphragm 116 against the ring 124, and thereby seal the associated valve port 122A. This closes the valve station to liquid flow.

When in its retracted position, the piston 290 does not apply force against the diaphragm 116. As before described, the plastic memory of the diaphragm 116 unseats it from the valve ring 124 (as FIG. 8 shows), and thereby opens the valve station to liquid flow.

The pressure sensing transducers PS1 to PS4 sense liquid pressures in the sensing stations S1 to S4. The sensed pressures are transmitted to the controller 246 as part of its overall system monitoring function.

(iii) The Cassette Pumping Module

As FIGS. 14 and 15 show, in the illustrated and preferred embodiment, each cassette pumping module 254 includes a pair of peristaltic rotor assemblies 292. The rotor assemblies 292 face each other at opposite ends of the valve assembly 286.

A rear wall 294 extends about half way around the back side of each rotor assembly 292 (see FIGS. 14 and 15). The space between the rear wall 294 and the rotor assembly 292 forms a pump race 296. When the cassette 22A is gripped by the elements 256, the tubing loops 134 and 136 extend into the pump race 296 (as FIG. 16 shows).

Figure 16:
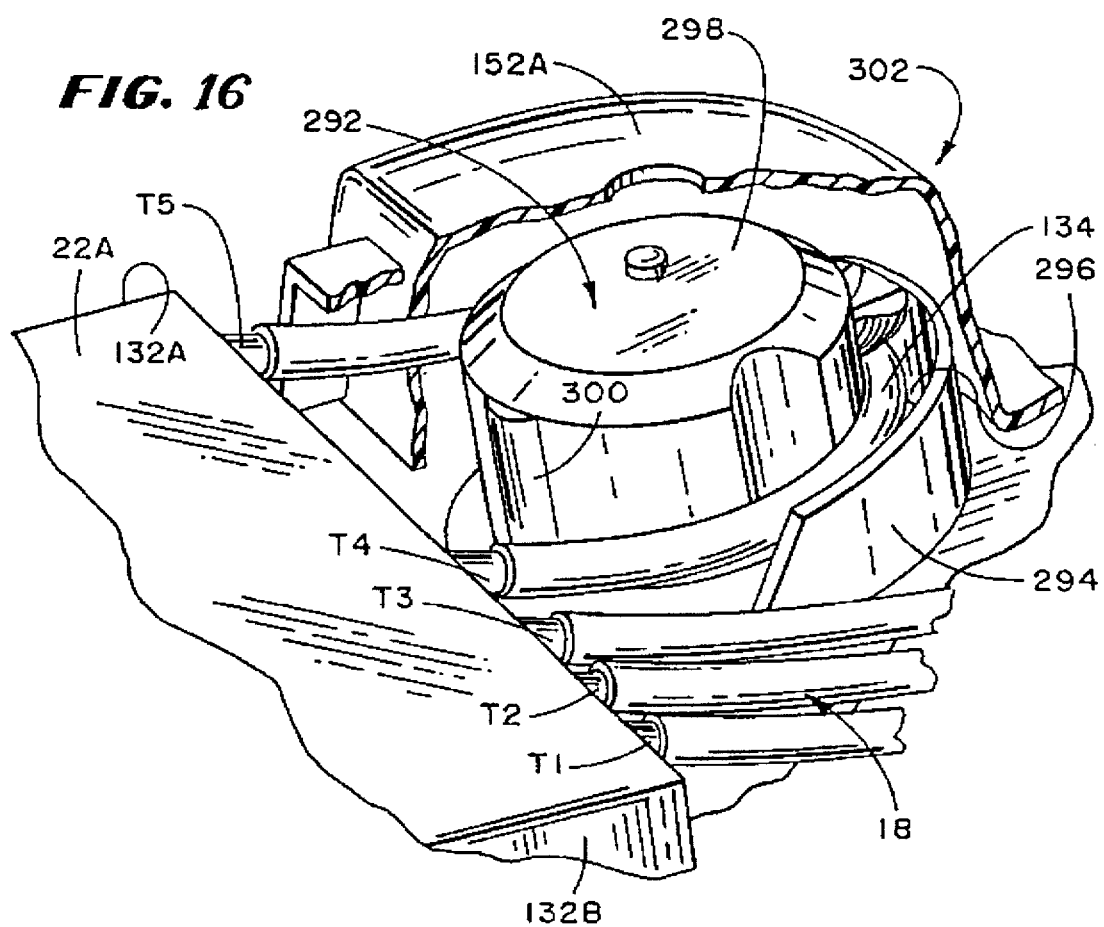
FIG. 16 is enlarged perspective view of the one pump module with the pump tubing installed.

As FIG. 16 shows, and as before described, the tube connectors T4/T5 and T6/T7 from which the loops 134 and 136 extend slope in the direction the pump rotor assemblies 292 to orient the loops 134 and 136 relative to the race 296 while loading the cassette 22A onto the station 236A.

Referring back to FIGS. 14 and 15, each rotor assembly 292 includes a rotor 298 that carries a pair of diametrically spaced rollers 300. In use, as the pump rotor 298 rotates, the rollers 300 in succession compress the associated tubing loop 134/136 against the rear wall 294 of the pump race 296 (as FIG. 43 shows). This well known peristaltic pumping action urges fluid through the associated loop 134/136.

Figure 17:
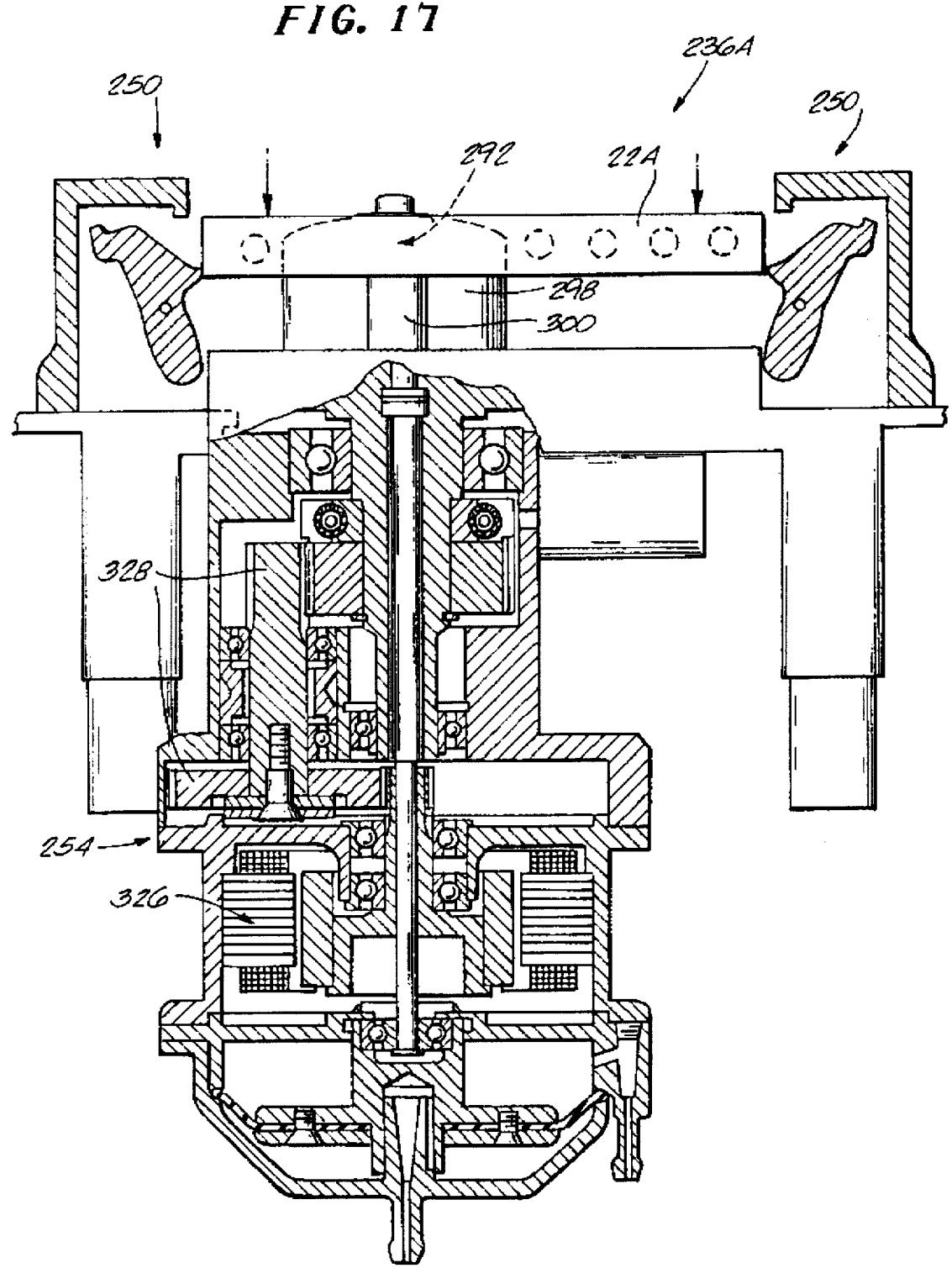
FIG. 17 is an elevated side section view showing the interior of an associated pump module.

As FIG. 17 shows, a small brushless direct current motor 326 drives each peristaltic pump rotor 298. A gear assembly 328 couples the motor 326 to the associated rotor 298.

Additional specific details of the construction of the pump rotor assembly 292 are not essential to an understanding of the invention and can be found in copending U.S. patent application Ser. No. 08/175,204, filed Dec. 22, 1993 and entitled "Peristaltic Pump with Linear Pump Roller Positioning Mechanism," which is incorporated herein by reference.

In a preferred embodiment, each pump rotor assembly 292 just described measures about 2.7 inches in diameter and about 6.5 inches in overall length, including the motor 326.

The pump rotor assembly 292 needs to operate at both relatively high flow rates (between 10 ml/min and 170 ml/min) and relatively low flow rates (i.e., less than 10 ml/min). The high flow rates are needed, for example, to supply WB to the processing chamber 26 (typically at about 50 ml/min) and to circulate saline and/or PPP to purge the tubing branches after processing (typically at about 100 ml/min, or higher).

Figure 10:
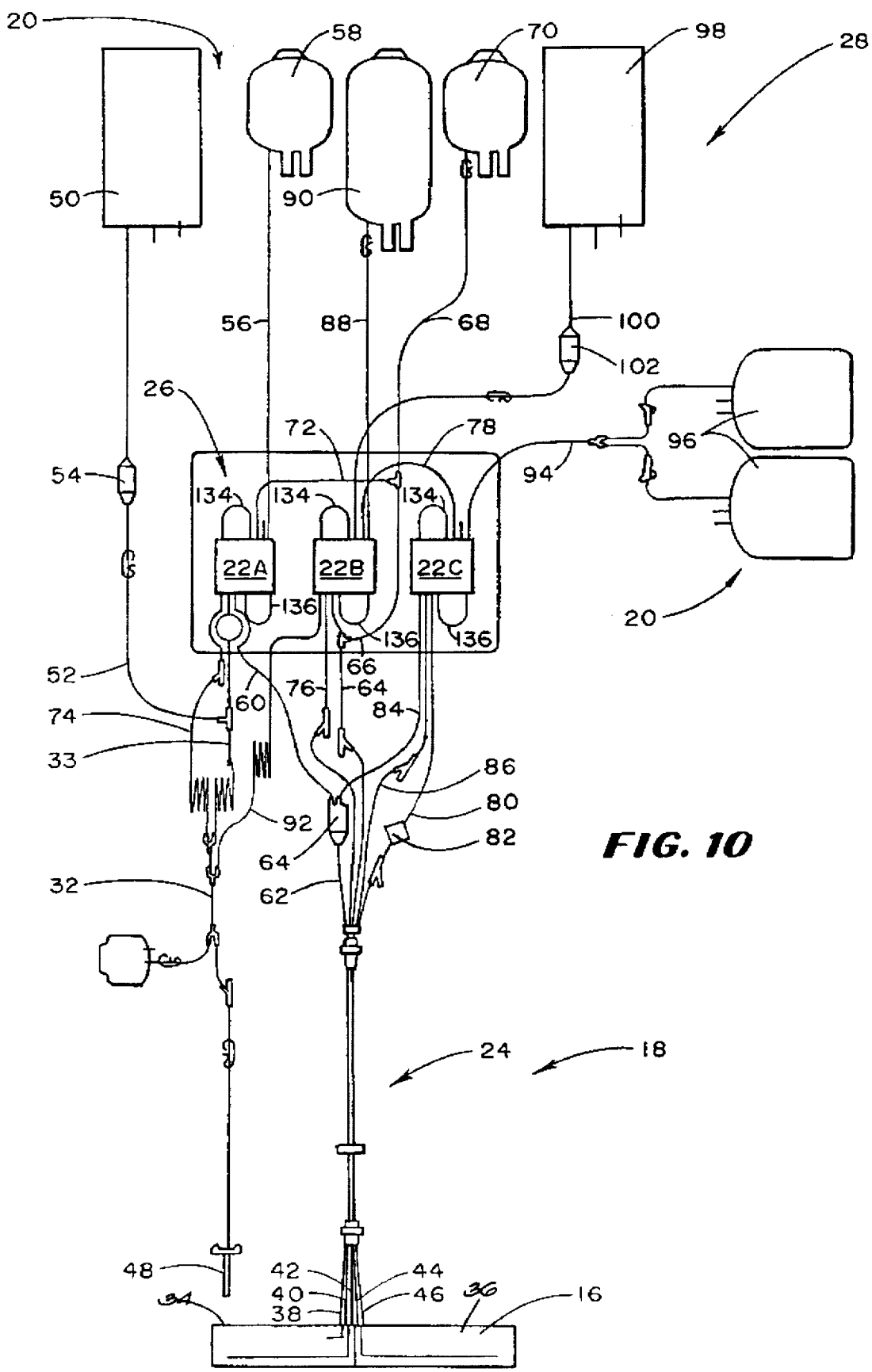
FIG. 10 is a diagrammatic view of a representative single needle fluid processing assembly usable in association with the centrifuge assembly shown in FIG. 1.

Relatively low flow rates are needed, for example, when conveying anticoagulant through tubing branch 100 (in the single needle system shown in FIG. 10). This is because a wide range of donor reactions can occur if too much anticoagulant is added, as this anticoagulant is ultimately returned to the donor with the reinfused plasma.

Relatively low flow rates are also needed, for example, when recirculating a portion of the PRP from the first stage compartment 34 back to the WB entering the compartment (through tubing branch 34 to the drip chamber 64 in the single needle system shown in FIG. 10).

The controller 246 operates the pump rotor assembly 292 in two modes. The first is a continuous mode, in which the pump rotor rotates continuously at an angular velocity selected to achieve the desired flow rate. The minimum continuous flow rate that the pump rotor assembly 292 maintains in the first mode is about 10 ml/min. The maximum continuous flow rate can be as high as about 170 ml/min.

When flow rates below the minimum continuous flow rate are required, the controller 246 operates the pump rotor assembly 292 in an intermittent, or pulse, mode. In the pulse mode, the controller 246 controls power to the brushless motor 326 to achieve desired first angular velocity for a first selected time period, followed in succession by at least one additional time period during which power is controlled to achieve a second angular velocity different than the first angular velocity.

The selected second angular velocity can be greater than or less than the first angular velocity. The second angular velocity can also be in an opposite direction than the first angular velocity, if desired to pulse fluid back and forth.

In the preferred implementation, the second angular velocity is at or near zero, so that rotation of the pump rotor 298 actually or essentially stops for the second time period. In this implementation, after the second time period, the controller 246 successive controls power to achieve a third angular velocity that is above zero and is preferably equal to the first angular velocity, for a third time period, followed in succession by a fourth time period during which rotation of the rotor 298 actually or essentially stops, and so on.

Establishing this sequence of setting the angular velocity at a selected amount for a time period, then at or about zero for another time period, the controller 292 achieves intermittent periods of rotation of the rotor 298, spaced by intervals in which the rotor 298 stops rotating.

By selecting an angular velocity (in terms of a desired RPM) and the time intervals during which the rotor 298 is on (i.e., rotating) and off (i.e., not rotating), the controller 292 can operate the pump rotor assembly 292 in a range of low flow rates well below the minimum continuous flow rate.

The effective flow rate $R_{EFF}$ of the pump rotor assembly 292 (in ml/min) when operated in the pulse mode can be expressed as follows:

$$R_{EFF} = \frac{T_{ON}}{T_{OFF}} (RPM)(k)$$

where:

$T_{ON}$ is the time interval (in seconds) that the rotor 298 rotates, $T_{OFF}$ is the time interval (in seconds) that the rotor 298 does not rotate, RPM is the rotor speed during rotation (in revolutions per minute), and k is the pump flow constant of the particular pump rotor assembly (in ml/revolution).

In implementing the pulse mode, the controller 246 sets a desired RPM and turns the pump motor 326 on and off in sequential pulses timed to achieve the desired flow rate. Typically, during each period in which the rotor 298 is turned on, the rotor 298 rotates less than one complete revolution. By pulsing in this manner, the controller 246 achieves flow rates that are well below the minimum continuous flow rate of the pump rotor assembly 292.

In the illustrated and preferred embodiment, in the pulse mode, the controller 292 sets the desired RPM to achieve the minimum continuous flow rate (which, in the illustrated embodiment is 10 ml/min). The timing of the pulses falls within the range of between about 0.3 second to 2.7 seconds. By varying the on and off times, the controller 246 provides effective flow rates of between about 1.0 and 9 ml/min.

The controller 246 includes a look up table in non-volatile memory that correlates, based upon empirical data that takes into account the particular pump flow constant and the selected RPM, the desired pumping rate with pulse on and pulse off time periods. A representative look up table, based upon a minimum continuous RPM of 10 ml/min, is shown below:

| Command $R_{EFF}$ (in ml/min) | $T_{ON}$ (in secs.) | $T_{OFF}$ (in secs.) |
|---|---|---|
| 1 | 0.3 | 2.7 |
| 2 | 0.3 | 1.2 |
| 3 | 0.3 | 0.7 |
| 4 | 0.4 | 0.6 |
| 5 | 0.5 | 0.5 |
| 6 | 0.6 | 0.4 |
| 7 | 0.7 | 0.3 |
| 8 | 1.2 | 0.3 |

-continued

| Command $R_{EFF}$ (in ml/min) | $T_{ON}$ (in secs.) | $T_{OFF}$ (in secs.) |
|---|---|---|
| 9 | 2.7 | 0.3 |

The just described implementation is best achieved when the pump rotor assembly 292 has a relatively high torque. In this way, the rotor 298 achieves the desired angular velocity in a short period of time when power is applied, while at the same time stopping rotation in a short period of time when power is interrupted. There are alternative ways to achieve equivalent pulse mode operation. For example, the controller could apply continuous power to a direct current stepper motor while changing the commutation patterns to electrically lock and unlock the rotor. As another example, the controller could employ a mechanical brake in combination with the interruption of power to quickly stop rotation of the rotor when desired.

Various features of the invention are set forth in the following claims.

We claim:

1. A peristaltic pumping apparatus comprising a peristaltic pumping element including a pump rotor carrying a rotor for contacting a flexible tubing, and a drive mechanism for rotating the rotor, and a control mechanism coupled to the drive mechanism and a power source, the control mechanism being sequentially operative (i) in a continuous mode for controlling power to the drive mechanism to continuously rotate the pump rotor more than one complete revolution at a first angular velocity selected to achieve a first selected flow rate, and (ii) in an intermittent mode for controlling power to the drive mechanism to rotate the pump rotor in a series of pulses, each pulse having a preestablished first time period, during which the pump rotor rotates less than one complete revolution at a selected second angular velocity less than the first angular velocity and a preestablished second time period immediately following the first time period, during which rotation of the rotor ceases, the series of pulses providing a second selected flow rate less than the first selected flow rate.

\* \* \* \* \*

UNITED STATES PATENT AND TRADEMARK OFFICE
CERTIFICATE OF CORRECTION

PATENT NO.    :   5,538,405
DATED         :   July 23, 1996
INVENTOR(S)   :   Patno et al.

It is certified that error appears in the above-identified patent and that said Letters Patent is hereby corrected as shown below:

Column 5, Line 52     "for mounted" should read --- for mounting ---

Column 6, Line 60     Delete "a" before "single"

Column 11, Line 44    Insert --- of --- before "the pump"

Column 12, Line 48    "successive" should read --- successively ---

Signed and Sealed this

Twenty-fifth Day of February, 1997

Attest:

BRUCE LEHMAN

Attesting Officer        Commissioner of Patents and Trademarks